United States Patent [19]

Pletcher

[11] Patent Number: 4,522,590
[45] Date of Patent: Jun. 11, 1985

[54] RING FOR ORTHODONTIC BRACKET

[76] Inventor: Erwin C. Pletcher, P.O. Box 3054, Rancho Sante Fe, Calif. 92067

[21] Appl. No.: 581,302

[22] Filed: Feb. 17, 1984

[51] Int. Cl.³ .............................................. A61C 7/00
[52] U.S. Cl. ..................................................... 433/15
[58] Field of Search ......................................... 433/15

[56] References Cited

U.S. PATENT DOCUMENTS 2,767,469 10/1956 Gladstone ............................ 433/11
3,461,558 8/1969 Miller et al. ......................... 433/15

*Primary Examiner*—Robert Peshock
*Attorney, Agent, or Firm*—Christie, Parker & Hale

[57] ABSTRACT

A wire ring which can be fitted over tie wings of an orthodontic bracket, and then twisted into tight engagement with the bracket. A resulting twisted tail of the ring provides a hook and eyelet for anchoring auxiliary appliances such as springs or elastics to the bracket. If fitted over an arch wire engaged in the bracket, the ring also provides secure ligating of the arch wire to the bracket.

13 Claims, 7 Drawing Figures

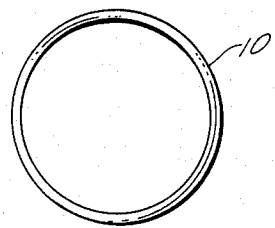
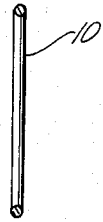
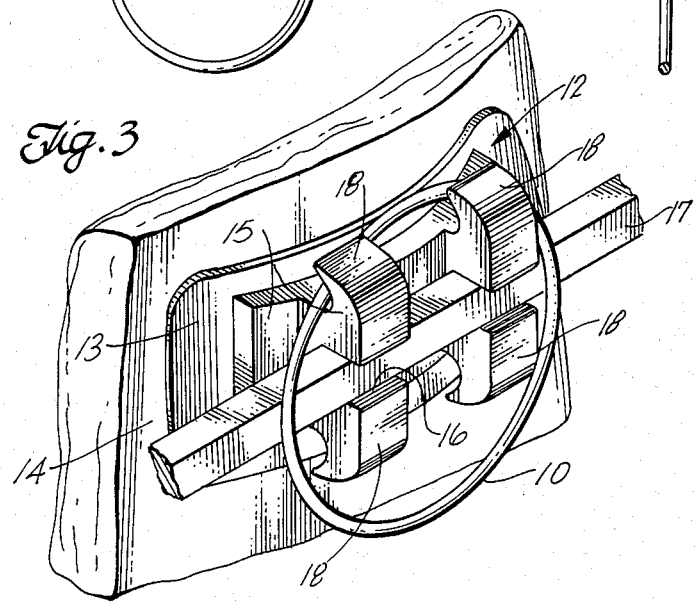
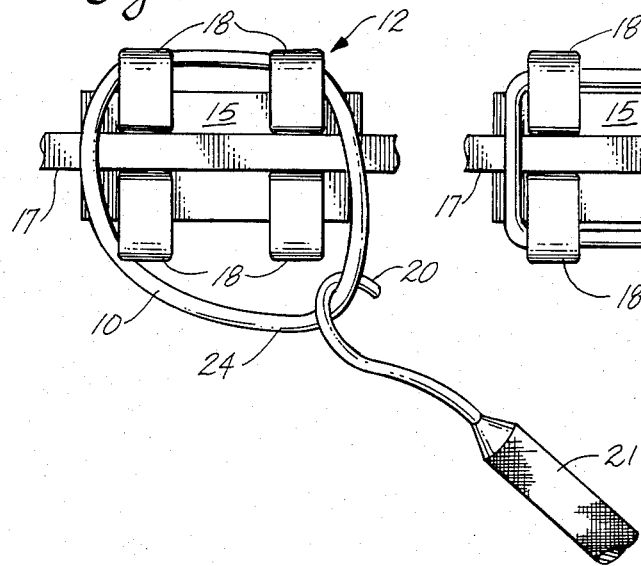
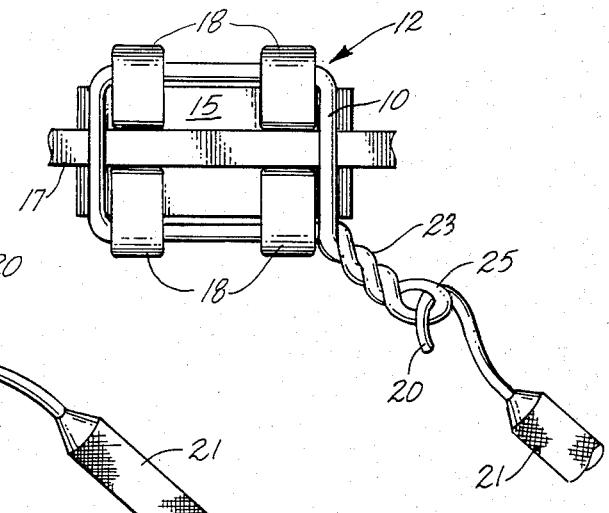

RING FOR ORTHODONTIC BRACKET

BACKGROUND OF THE INVENTION

Orthodontic treatment of improperly positioned teeth involves the application of mechanical forces to urge the teeth into correct alignment. The most common form of treatment involves use of orthodontic brackets which are small slotted bodies configured for direct cemented attachment to the front (labial) or rear (lingual) surfaces of the teeth, or alternatively for attachment to bands which are in turn cemented or otherwise secured around the teeth.

A resilient curved arch wire is seated in the bracket slots, and the arch wire is bent or twisted before installation so the restoring force exerted by the seated resilient wire tends to shift the teeth into correct alignment. Depending on the shape of the arch wire (both round and rectangular cross sections are in common use) and the orientation of the bracket slot, it is possible to apply forces which will shift, rotate or tip the teeth in any desired direction.

Conventional orthodontic brackets include tie wings around which small ligature wires are tied to hold the arch wire in a securely seated position in the brackets. Ligatures or some other form of fastening means are essential to insure that the activated arch wire is properly positioned around the dental arch, and to prevent the wire from being dislodged from the bracket slots during chewing of food, brushing of the teeth, or application of other forces to the wire by the patient.

During one or more stages of an overall orthodontic treatment program, it is often desirable to use auxiliary appliances to supplement or replace the corrective force supplied by the arch wire. Metal springs or elastic bands or threads are typical auxiliary devices used for this purpose, and they must be anchored at their ends to spaced-apart brackets to apply the desired restoring force to the teeth.

Auxiliary-appliance anchorage is usually provided by welding or soldering a wire hook, cleat, button, or eyelet to a bracket or directly to the arch wire. Installation of this kind of anchor is time consuming for the orthodontist, and, with the exception of crimpable anchors, usually must be fitted prior to installation of brackets and arch wires on the patient's teeth.

Another style of anchor is a special ligature which is a U-shaped hairpin-like length of ligature wire having generally parallel legs which are welded together close to the base of the "U" configuration to form a small closed loop in which an auxiliary appliance can be hooked. This ligature is as time consuming to install as a conventional ligature wire, and has the usual twisted and severed tail which must be carefully tucked against the bracket to avoid tissue contact and irritation.

The ring of this invention is in retrospect a very simple structure which provides hook and eyelet anchorage for an auxiliary appliance, and can also serve as a clean, nonirritating ligature to secure the arch wire to the bracket. The ring is a continuous loop of stainless-steel wire dimensioned to fit over the bracket tie wings. When so fitted, the ring is quickly and easily twisted to be tightened against the bracket, and to provide a smooth (no sharp ends) tail which is bent to form the desired hook or eyelet anchorage.

SUMMARY OF THE INVENTION

Briefly stated, this invention relates to an endless loop of wire configured to fit over and be contracted by twisting into engagement behind tie wings of an orthodontic bracket. The loop or ring is preferably made of a soft or annealed stainless-steel wire. When installed, the twisted portion forms a tail which can be curved into an auxiliary-appliance hook, and which also provides a terminal eyelet in which the end of such an appliance can be engaged. In a modified form, the ring may be bent into a shallow "V" shape for easy fitting on the bracket, and may also include a short length of plastic resilient tubing which serves as a rotation bumper when the ring is installed beneath an arch wire seated in the bracket.

BRIEF DESCRIPTION OF THE DRAWINGS

FIG. 1 is an elevation of a ring according to the invention;

FIG. 2 is a side sectional view of the ring;

FIG. 3 is a pictorial view of the ring loosely engaged with an orthodontic bracket;

FIG. 4 is an elevation similar to FIG. 3, but with a hooked tool positioned to begin the ring installation;

FIG. 5 is a view similar to FIG. 4, but with the ring fully twisted;

DESCRIPTION OF THE PREFERRED EMBODIMENTS

Figure 6:
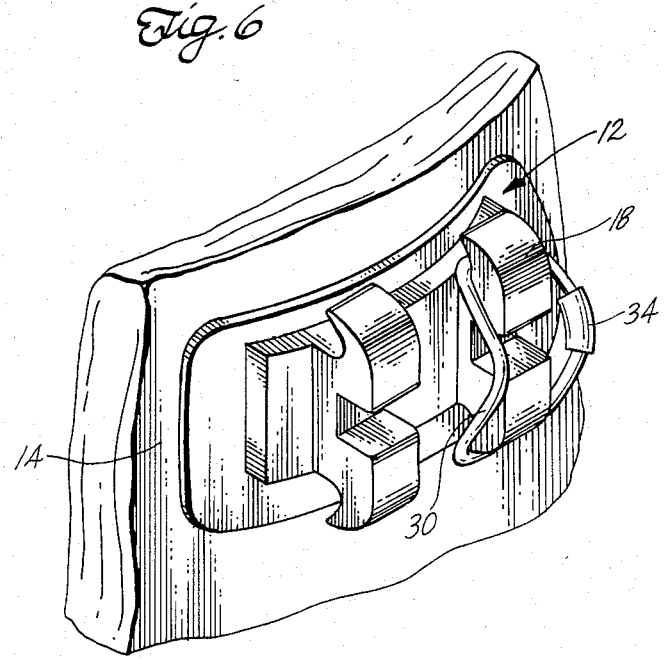
FIG. 6 is a pictorial view of a pre-bent ring which includes a plastic tube serving as a rotation device.

Referring to FIGS. 1 and 2, an orthodontic-bracket ring 10 of this invention is preferably initially formed as an endless circular loop of stainless-steel (the type used to make conventional orthodontic ligature wires is satisfactory) round wire having a cross-sectional diameter of about 0.010 to 0.014 inch. The ring is provided in a range of internal diameters to fit over brackets of various sizes as described below, and this diameter is typically in the range of about one-eighth to one-fourth inch. The wire is soft and formable, and may be annealed if necessary to achieve these properties.

In one form, ring 10 is made by forming a circle from a length of wire, and lap or butt welding the wire ends together. Another manufacturing method is to cut rings from the end of a length of stainless-steel tubing of appropriate inside diameter and wall thickness. This cutting operation can be done on automatic production machines at high speed, and the resulting rings are then tumbled, or electropolished, or otherwise processed to eliminate any sharp surfaces resulting from the machining process.

A conventional twin-wing orthodontic bracket 12 is shown in FIG. 3, and the bracket includes a base 13 for cemented attachment to the surface of a tooth 14. The bracket may also be of a style which is welded to a conventional tooth band (not shown) for cemented attachment to the tooth.

A bracket body 15 extends away from the tooth and bracket base, and the body defines a slot 16 to receive a conventional arch wire 17 which extends around the patient's dental arch. Two pairs of tie wings 18 extend rearwardly from the end of the bracket body on opposite sides of the arch wire.

Ring 10 is shown in FIG. 3 as loosely fitted over and behind the upper tie wings of the bracket, and is easily positioned in this manner with the fingers or a tweezer or plier. A curved hook-like tip 20 of a twisting tool 21 (a conventional handheld dental explorer, modified to provide the curved tip, is quite satisfactory) is then fitted within the ring as shown in FIG. 4. The tool is drawn laterally away from the bracket body to pull the ring around the lower tie wings by slight deformation of the original circular shape of the ring.

Tool 21 is then rotated to form a twisted tail 23 in ring 10 to contract the ring tightly around the bracket body behind the tie wings as shown in FIG. 5. The tool is rotated counterclockwise to draw a free portion 24 (FIG. 4) of the ring inwardly toward the bracket base beneath the adjacent tie wing. The twisting operation is completed in a few seconds, and the tool tip is then removed from the resulting small eyelet 25 at the end of tail 23.

The twisted tail of the installed ring can be bent into any desired hook shape. The resulting hook provides an anchor for an auxiliary appliance such as an elastic band which extends to a similar anchor on another tooth (not shown). Eyelet 25 also provides an anchor for the hooked end of a different style of auxiliary appliance such as a wire coil spring (not shown).

Twisting of ring 10 to form tail 23 work hardens the stainless-steel wire forming the ring, providing desired rigidity to the tail. In contrast to conventional ligature wires which have sharp cut ends after being installed, tail 23 is smooth and endless, and the risk of irritation or cutting of the patient's gums or cheek tissue is minimized.

When ring 10 is fitted over arch wire 17 as shown in FIGS. 3–5, the installed ring provides secure ligating of the arch wire to the bracket, and the ring is useful for this purpose alone. The ring may thus be used solely as a physiologically clean and nonirritating ligature which can be installed more easily and quickly than a conventional ligature wire, but it also provides the twisted tail as an anchor for auxiliary appliances.

Ring 10 can also be fitted beneath the arch wire if the ligating function is unnecessary (as will be the case if the bracket provides another style of arch-wire securing means such as the locking brackets shown in my U.S. Pat. Nos. 4,077,126, 4,371,337 and 4,419,078. In this case, the ring is twisted in place before the arch wire is seated (FIGS. 7 and 8), and the purpose of the ring is only to provide hook or eyelet anchorage for an auxiliary appliance.

Although installation of a flat ring 10 as described above is simple, an alternative procedure is provided by use of a modified ring 30 as shown in FIG. 6. Ring 30 is identical to ring 10, except for being bent into a shallow "V" shape about its diameter. This curvature places the upper and lower parts of the ring behind tie wings 18, eliminating the slight preliminary manipulation of the ring prior to twisting of ring tail 31.

As suggested in FIG. 6, it is not necessary to secure the ring around all of the bracket tie wings, and ring 30 is shown as engaged with only one set of upper and lower tie wings 18 on twin-wing bracket 12. The ring is equally useful on single-wing brackets in a variety of different styles. The tie wings need not be of the specific shape shown in the drawings, and this term is intended to apply to any equivalent retaining ledge, shoulder, or the like on the bracket body.

Figure 7:
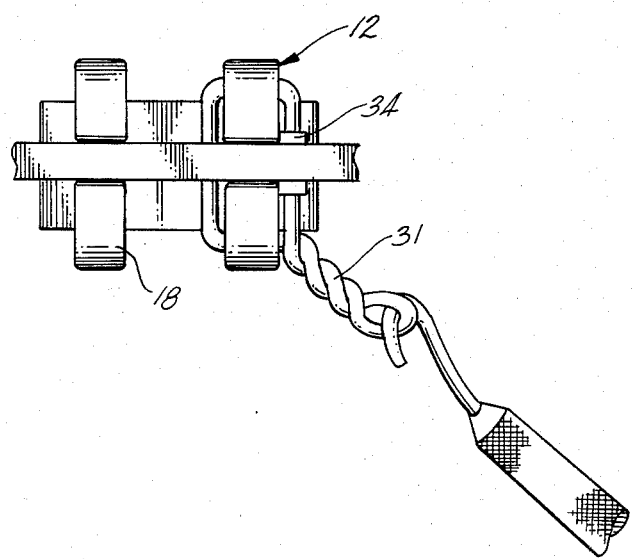
FIG. 7 is an elevation of a bracket showing the ring of FIG. 6 installed under an arch wire.

An additional feature of the ring of this invention is shown in FIGS. 6 and 7 in that a short section of slightly resilient plastic tubing 34 (nylon is a suitable material) is threaded on or fitted over the ring prior to installation on the bracket. The tubing is positioned and compressed beneath the subsequently seated arch wire (FIG. 7) to serve as a rotation bumper which imposes a rotation force on a tooth needing this mode of corrective movement.

The ring of this invention is quite compact, and normally occupies only a portion of the space behind the tie wings. In cases where the ring is fitted behind the arch wire as in FIG. 7, the tie wings can thus still be used to anchor a second ring or a conventional ligature wire to secure the arch wire to the bracket.

Rings 10 and 30 are especially convenient to use on lingual brackets which are mounted on the rear or inner tooth faces. This bracket positioning (which is of growing popularity for cosmetic reasons because the brackets are less visible) limits the space available for use of pliers to twist conventional ligature wires in place, but a compact tool such as tool 21 is easily inserted behind the teeth to twist and contract a ring of this invention around a lingual bracket. A needle-nose hemostat or small pointed locking plier is also useful to handle and install the ring.

Rings according to the invention need not be precisely circular prior to installation (an oval shape, for example, is quite acceptable), but should be configured for the convenient "loose" preliminary fitting behind the bracket tie wings prior to twisting. The circular configuration is preferred as a matter of manufacturing convenience, and because it is easily fitted over most styles of orthodontic brackets. The ring is easily made in a variety of internal diameters to insure compatibility with all conventional styles and sizes of orthodontic brackets.

There has been described a simple and effective ring for use with an orthodontic bracket to provide ligating and anchoring functions. In spite of its simplicity, the ring is a significant improvement over conventional ligature wires and separate anchors for auxiliary appliances.

What is claimed is:

1. A ring for use with an orthodontic bracket with tie wings, comprising an endless loop of stainless-steel wire dimensioned to fit over the bracket tie wings, the wire being sufficiently soft to enable permanent-deformation twisting of a portion of the loop to reduce the length of the ring and thereby to tighten the ring against the bracket behind the tie wings, and to provide a twisted tail as an anchor for an auxiliary appliance.

2. The ring defined in claim 1 wherein the wire has a generally circular cross section with a diameter in the range of about 0.010 to 0.014 inch.

3. The ring defined in claim 2 wherein the ring is substantially circular with an inside diameter in the range of about one-eighth to one-quarter inch.

4. The ring defined in claim 1, and further comprising a short resilient tube fitted on the loop to be positioned behind an arch wire on the bracket as a rotation device.

5. The ring defined in claim 1, wherein an initially circular loop is bent into a shallow V-shape as viewed from the side to be readily engaged with opposed tie wings on the bracket.

6. The ring defined in claim 1 wherein the endless loop is formed by welding adjacent ends of a length of stainless-steel wire bent into a generally circular configuration.

7. The ring defined in claim 1 wherein the endless loop is formed by severing an end portion from a stainless-steel tube, and subsequently polishing the resulting loop to provide a smooth surface.

8. The ring defined in claim 1 wherein an end of the twisted tail remote from the tightened loop defines an eyelet.

9. In combination with an orthodontic bracket having tie wings on opposite sides of an arch-wire slot, and an arch wire extending through the slot, an endless loop of formable metal wire fitted over the tie wings in contact with the arch wire, the loop having a twisted portion which reduces the loop length to tighten the loop against the bracket, the twisted portion forming an anchor for an auxiliary appliance.

10. The combination defined in claim 9 wherein the wire is stainless steel.

11. The combination defined in claim 10 wherein the wire has a diameter in the range of about 0.010 to 0.014 inch.

12. The combination defined in claim 11 wherein the twisted portion terminates in a closed eyelet.

13. In combination with an orthodontic bracket having tie wings on opposite sides of an arch-wire slot, and an arch wire extending through the slot, a ligature ring formed of an endless loop of soft formable stainless-steel wire having an original loop length enabling the ring to be fitted over the tie wings and arch wire, the fitted loop having a twisted portion which reduces the original loop length to a smaller length to tighten the loop against the bracket behind the tie wings to hold the arch wire in the slot.

* * * * *